United States Patent
Takeuchi et al.

(10) Patent No.: US 8,080,570 B2
(45) Date of Patent: Dec. 20, 2011

(54) α2B AND α2C AGONISTS

(75) Inventors: Janet A. Takeuchi, Anaheim, CA (US);
Ken Chow, Newport Coast, CA (US);
Ling Li, Irvine, CA (US); Liming Wang, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 246 days.

(21) Appl. No.: 12/433,953

(22) Filed: May 1, 2009

(65) Prior Publication Data

US 2009/0275627 A1 Nov. 5, 2009

Related U.S. Application Data

(60) Provisional application No. 61/050,367, filed on May 5, 2008.

(51) Int. Cl.
*A01N 43/76* (2006.01)
*A61K 31/42* (2006.01)
*C07D 413/00* (2006.01)
*C07D 263/00* (2006.01)

(52) U.S. Cl. ........................ 514/377; 548/233
(58) Field of Classification Search .................. 514/377; 548/233
See application file for complete search history.

(56) References Cited

FOREIGN PATENT DOCUMENTS

WO WO 92/00073 1/1993
WO WO 03/075922 9/2003

OTHER PUBLICATIONS

Kowal, Dianne; et al.: Functional Calcium Coupling with the Human Metabotropic Glutamate Receptor Subtypes 2 and 4 by Stable Co-Expression with a Calcium Pathway Facilitating G-Protein Chimera in Chinese Hamster Ovary Cells. Biochemical Pharmacology 66, 2003, pp. 785-790.
Serrano, M.I.; et al.: Synthesis and Analgesic Activity of 2-Amino-5-tert-butyl-2-oxazoline, Arzneimittel-Forschung, 45(1), 22-6 Coden: Arznad.
Silverman, Richard B.: prodrugs and Drug Delivery Systems, Organic Chemistry of Drug Design and Drug Action, 2d Ed., Elsevier Academic Press: Amsterdam, 2004, pp. 496-557.
Ueda, Shigeo; et al.: 4,5-Disubstituted-1,3-oxazolidin-2-imine Derivatives: a New Class of Orally Bioavailable Nitric Oxide Synthase Inhibitor, Bioorganic & Medicinal Chemistry Letters 14(2004) 313-316.

*Primary Examiner* — Marcos Sznaidman
(74) *Attorney, Agent, or Firm* — Doina G. Ene; John E. Wurst; Kevin J. Forrestal

(57) ABSTRACT

Described herein are compounds that can be useful as bioactive agents. More specifically, the compounds described herein can be useful as both $\alpha_{2B}$ and $\alpha_{2C}$ adrenergic agonists. Methods of synthesis and administration of the compounds are also disclosed.

2 Claims, No Drawings

α2B AND α2C AGONISTS

RELATED APPLICATION

This application claims the benefit of U.S. Provisional Application Ser. No. 61/050,367, filed May 5, 2008, the disclosure of which is hereby incorporated in its entirety herein by reference

FIELD OF THE INVENTION

The present invention relates to the synthesis and administration of novel compounds useful as $\alpha_{2B}$ and $\alpha_{2C}$ adrenergic agonists.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$ and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having $\alpha_2$ adrenergic receptor agonist activity are known analgesics. However, many compounds having such activity do not provide the activity and specificity desirable when treating disorders modulated by $\alpha_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

SUMMARY OF THE INVENTION

Described herein are compounds that can be useful as bioactive agents. More specifically, compounds as described herein can be useful as $\alpha_{2B}$ and $\alpha_{2C}$ adrenergic agonists. Methods of synthesis and administration of the compounds are disclosed.

In one embodiment, bioactive agent is described for administration to a mammal comprising a compound represented by the formula 1:

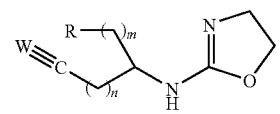

Formula 1 wherein n is 0 or 1; m is 0 or 1-10; W is CH or N; R is a $C_{1-10}$ alkyl, a substituted or unsubstituted aryl or heteroaryl; and pharmaceutically acceptable salts, and combinations thereof. In one embodiment, n is 0 or 1.

In one embodiment, the substituted or unsubstituted aryl or heteroaryl is selected from the group consisting of phenyl, pyridinyl, thienyl, furyl, naphthyl, quinolinyl, indanyl or benzofuryl.

In another embodiment, the bioactive agent is an $\alpha_{2B}$ agonist. In another embodiment, the bioactive agent is an $\alpha_{2C}$ agonist. The bioactive agent can be used to treat a condition selected from the group consisting of hypertension, congestive heart failure, asthma, depression, glaucoma, elevated intraocular pressure, ischemic neuropathies, optic neuropathy, pain, visceral pain, corneal pain, headache pain, migraine, cancer pain, back pain, irritable bowel syndrome pain, muscle pain, pain associated with diabetic neuropathy, the treatment of diabetic retinopathy, other retinal degenerative conditions, stroke, cognitive deficits, neuropsychiatric conditions, drug dependence, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's disease, Parkinson's disease, amyotrophic lateral sclerosis, and combinations thereof. In one embodiment, the bioactive agent is an analgesic.

In one embodiment, the bioactive agent is used to treat chronic pain. In another embodiment, the bioactive agent is administered at does of 1-1000 mg per day. In another embodiment, the bioactive agent is administered orally in one of the forms selected from the group consisting of tablets, liquid, capsules, powder, and combinations thereof. In another embodiment, the bioactive agent is administered according to a method selected from the group consisting of transdermally, parenterally, subcutaneously, intranasally, intrathecally, intramuscularly, intravenously, intrarectally, and combinations thereof.

In one embodiment, a method is described for treating a medical condition in a mammal comprising administration of a compound represented by formula 1:

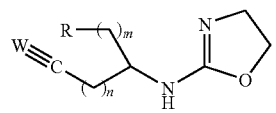

Formula 1 wherein n is 0 or 1; m is 0 or 1-10; W is CH or N; R is a $C_{1-10}$ alkyl, a substituted or unsubstituted aryl or heteroaryl; and pharmaceutically acceptable salts, and combinations thereof.

In one embodiment, the substituted or unsubstituted aryl or heteroaryl is selected from the group consisting of phenyl, pyridinyl, thienyl, furyl, naphthyl, quinolinyl, indanyl or benzofuryl.

In one embodiment, the compound is an $\alpha_{2B}$ agonist, in another embodiment, the compound is an $\alpha_{2C}$ agonist. In one embodiment, the medical condition is selected from the group consisting of hypertension, congestive heart failure, asthma, depression, glaucoma, elevated intraocular pressure, ischemic neuropathies, optic neuropathy, pain, visceral pain, corneal pain, headache pain, migraine, cancer pain, back pain, irritable bowel syndrome pain, muscle pain, pain associated with diabetic neuropathy, the treatment of diabetic retinopathy, other retinal degenerative conditions, stroke, cognitive deficits, neuropsychiatric conditions, drug dependence, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's disease, Parkinson's disease, amyotrophic lateral sclerosis, and combinations thereof. In one embodiment, the compound is an analgesic.

In one embodiment, the compound is used to treat chronic pain. In another embodiment, the compound is administered at does of 1-1000 mg per day. In one embodiment, the compound is administered orally in one of the forms selected from the group consisting of tablets, liquid, capsules, powder, and combinations thereof. In another embodiment, the administration of the compound is a method selected from the group consisting of transdermally, parenterally, subcutaneously, intranasally, intrathecally, intramuscularly, intravenously, intrarectally, and combinations thereof.

In another embodiment, the compound and/or bioactive agent is selected from the group consisting of:

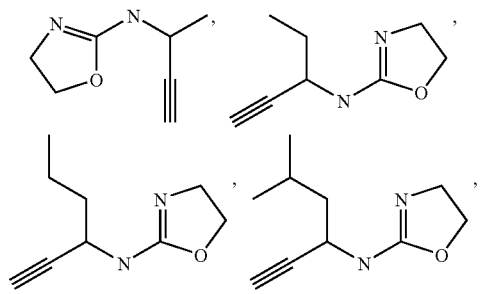

-continued

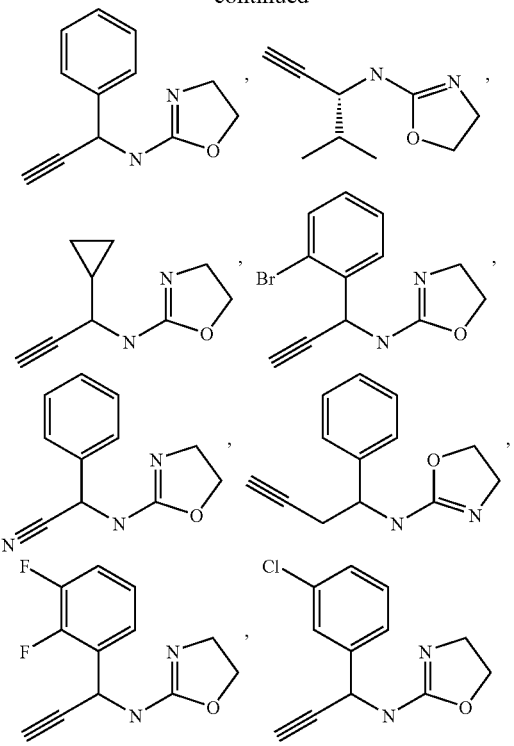

, salts, and combinations thereof.

DEFINITION OF TERMS

Prodrug: A "prodrug" is a compound which is converted to a therapeutically active compound after administration. While not intending to limit the scope of the invention, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Halogen: As used herein, "halogen" is used to refer to a subsistent found in column VIIA of the periodic table of elements, including fluorine, chlorine, bromine, and iodine.

Tautomer: As used herein, "tautomer" refers to the migration of protons between adjacent single and double bonds. The tautomerization process is reversible. Compounds described herein can undergo the following tautomerization:

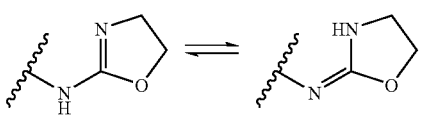

DETAILED DESCRIPTION OF THE INVENTION

The present description provides compounds useful as selective $\alpha_{2B}$ and $\alpha_{2C}$ agonists in mammals, including but not limited to, humans. The compounds may be substituted N-(alkynl)-4,5-dihydrooxoazol-2-amines.

The compounds may be represented by Formula 1:

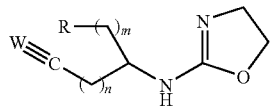

Formula 1 wherein n is 0 or 1-10; m is 0 or 1-10; W is CH or N; R is a $C_{1-10}$ alkyl, a substituted or unsubstituted aryl or heteroaryl; and pharmaceutically acceptable salts, and combinations thereof.

R can be a $C_{1-10}$ alkyl, which includes $C_{3-10}$ cycloalkyls and $C_{3-10}$ branched alkyls. R can also be a substituted or unsubstituted aryl or heteroaryl which can include aromatic, heteroaromatic, or multi-heteroaromatic groups. The substituted or unsubstituted aryl or heteroaryl can be selected from phenyl, pyridinyl, thienyl, furyl, naphthyl, quinolinyl, indanyl or benzofuryl. Exemplary substituted or unsubstituted aryls or heteroaryls include, but are not limited to, benzenes, pyridines, thiophenes, furans, naphthalenes, quinolines, indans and benzofurans. The aryl groups may be substituted with any common organic fictional group. Such aryl groups may be bonded to Formula 1 at any available position on the aryl group.

An exemplary aryl group is a benzene (Formula 2):

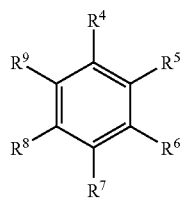

Formula 2 wherein at least one of $R^{4-9}$ must be Formula 1 and wherein the remaining $R^{4-9}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a pyridine as in Formula 3:

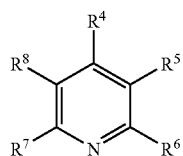

Formula 3 wherein at least one of $R^{4-8}$ must be Formula 1 and wherein the remaining $R^{4-8}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a thiophene as in Formula 4:

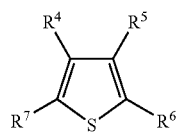

Formula 4 wherein at least one of $R^{4-7}$ must be Formula 1 and wherein the remaining $R^{4-7}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a furan as in Formula 5:

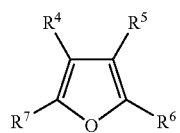

Formula 5 wherein at least one of $R^{4-7}$ must be Formula 1 and wherein the remaining $R^{4-7}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a naphthalene as in Formula 6:

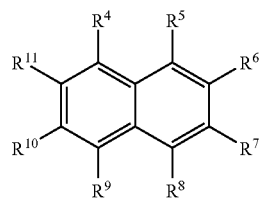

Formula 6 wherein at least one of $R^{4-11}$ must be Formula 1 and wherein the remaining $R^{4-11}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a quinoline as in Formula 7:

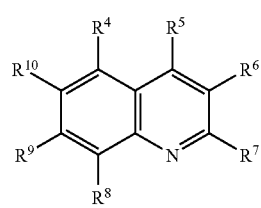

Formula 7 wherein at least one of $R^{4-10}$ must be Formula 1 and wherein the remaining $R^{4-10}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be an indan as in Formula 8:

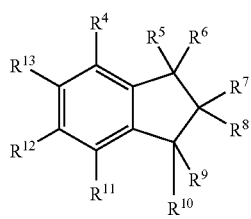

Formula 8 wherein at least one of $R^{4-13}$ must be Formula 1 and wherein the remaining $R^{4-13}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Another aryl group may be a benzofuran as in Formula 9:

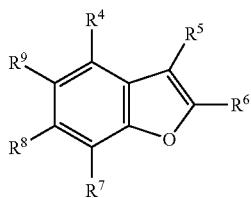

Formula 9 wherein at least one of $R^{4-9}$ must be Formula 1 and wherein the remaining $R^{4-9}$ may be each independently substituted with a common organic functional group including, but not limited to, hydrogen, a $C_{1-10}$ alkyl, $C_{1-10}$ alkenyl, $C_{1-10}$ alkynl, aryl, halogen, hydroxyl, alkoxy, amino, cyano, nitro, thiol, or carboxy group substituted with a $C_{1-10}$ alkyl, $C_{1-10}$ alkenyl, $C_{1-10}$ alkynl, aryl, halogen, hydroxyl, alkoxy, amino, cyano, nitro, or thiol group.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

Not intended to be limited by the above described compounds, various tautomers of the above compounds may be possible. For example, not intended as a limitation, tautomers are possible between the 4,5-dihydrooxazole and the adjacent nitrogen as shown below.

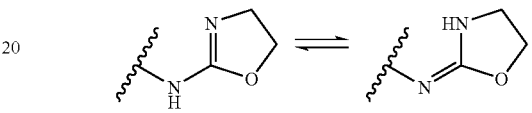

Other tautomers are possible when the compound includes, for example but not limited to, enol, keto, lactamin, amide, imidic acid, amine, and imine groups. Tautomers will generally reach an equilibrium state wherein the double bond is resonantly shared between the two bond lengths.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Selected examples were tested via the intracellular calcium assay known as Fluorometric Imaging Plate Reader (FLIPR) which involves the detection of calcium pulses by fluo-3 for analyzing function proximal to α1 receptor activation. Exemplary compounds of the invention are disclosed by their structural formulas in the following table together with their potency expressed in nanomolar (nM) as the concentration at which half of their maximal activity is observed ($EC_{50}$). The compound's activity is expressed as its relative efficacy compared to a standard full agonist.

| Structure | $\alpha_{2A}$ | $\alpha_{2B}$ | $\alpha_{2C}$ | $\alpha_{1A}$ | $\alpha_{1B}$ |
|---|---|---|---|---|---|
| 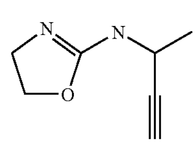 | 4047.01 (0.20) | 413.43 (0.77) | 34.62 (0.89) | >10000 | >10000 |

-continued
| Structure | α$_{2A}$ | α$_{2B}$ | α$_{2C}$ | α$_{1A}$ | α$_{1B}$ |
|---|---|---|---|---|---|
| 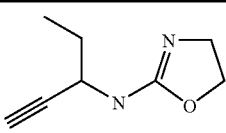 | 54.70 (0.74) | 91.52 (0.82) | 0.004 (0.87) | 6538.28 (0.78) | NA |
| 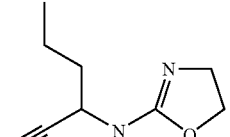 | 664.05 (0.44) | 386.40 (0.68) | 65.04 (0.99) | 3034.70 (0.72) | >10000 |
| 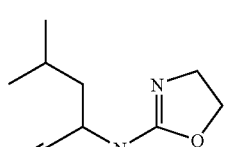 | >10000 | 330.51 (0.48) | 18.26 (0.98) | 7369.76 (0.59) | >10000 |
| 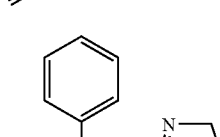 | 0.04 (0.82) | 1.12 (0.61) | Potent (0.82) | 0.58 (0.92) | 17.49 (0.87) |
| 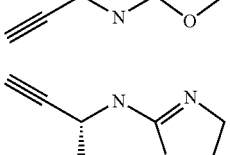 | 16.88 (0.85) | 63.99 (0.88) | Potent (1.02) | 1199.73 (0.93) | 5938.88 (0.28) |
| 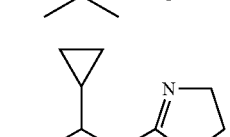 | 298.24 (0.41) | 353.55 (0.71) | 126.66 (0.89) | NA | >10000 |
| 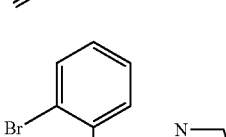 | >10000 | 361.44 (0.36) | 295.33 (0.81) | 1650.41 (0.34) | >10000 |
| 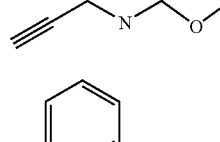 | 587.73 (0.42) | 215.14 (0.56) | 157.52 (0.76) | 1137.32 (0.99) | NA |
| 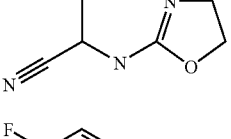 | 29.96 (0.79) | 25.86 (0.50) | 6.01 (0.88) | 40.82 (0.96) | 3507.01 (0.54) |

-continued

| Structure | $\alpha_{2A}$ | $\alpha_{2B}$ | $\alpha_{2C}$ | $\alpha_{1A}$ | $\alpha_{1B}$ |
|---|---|---|---|---|---|
| [Cl-phenyl propargyl oxazoline structure] | 80.48 (0.88) | 218.20 (0.56) | 382.45 (0.78) | 409.53 (0.81) | 5363.31 (0.24) |

NA = "not active"

The compounds described herein may be useful for the treatment of a wide range of therapeutic areas including, but not limited to, hypertension, congestive heart failure, asthma, depression, glaucoma, elevated intraocular pressure, ischemic neuropathies, optic neuropathy, pain, visceral pain, corneal pain, headache pain, migraine, cancer pain, back pain, irritable bowel syndrome pain, muscle pain, pain associated with diabetic neuropathy, the treatment of diabetic retinopathy, other retinal degenerative conditions, stroke, cognitive deficits, neuropsychiatric conditions, drug dependence, withdrawal symptoms, obsessive compulsive disorder, obesity, insulin resistance, stress related conditions, diarrhea, diuresis, nasal congestions, spasticity, attention deficit disorder, psychoses, anxiety, autoimmune disease, Crohn's disease, gastritis, Alzheimer's disease, Parkinson's disease, amyotrophic lateral sclerosis, and other neurodegenerative diseases.

Applicants have discovered that these compounds activate $\alpha_{2B}$ and $\alpha_{2C}$ receptors. Additionally, these compounds act as a highly effective analgesic, particularly in chronic pain models, with minimal undesirable side effects, such as sedation and cardiovascular depression, commonly seen with agonists of $\alpha_{2B}$ and $\alpha_{2C}$ receptors.

Such compounds may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds may be useful in the treatment of pain in a mammal, particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1, pharmaceutically acceptable derivatives, salts, prodrugs and/or combinations of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of a compound of Formula 1, and pharmaceutically acceptable salts, and derivatives thereof to a mammal in need thereof. As indicated above, the compound will usually be formulated in a form consistent with the desired mode of delivery.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acid/carboxylate), one or more protonated basic groups (e.g. amine/ammonium), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action*, 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

The following examples provide synthesis methods for forming compounds described herein. One skilled in the art will appreciate that these examples can enable a skilled artisan to synthesize the compounds described herein.

EXAMPLE 1

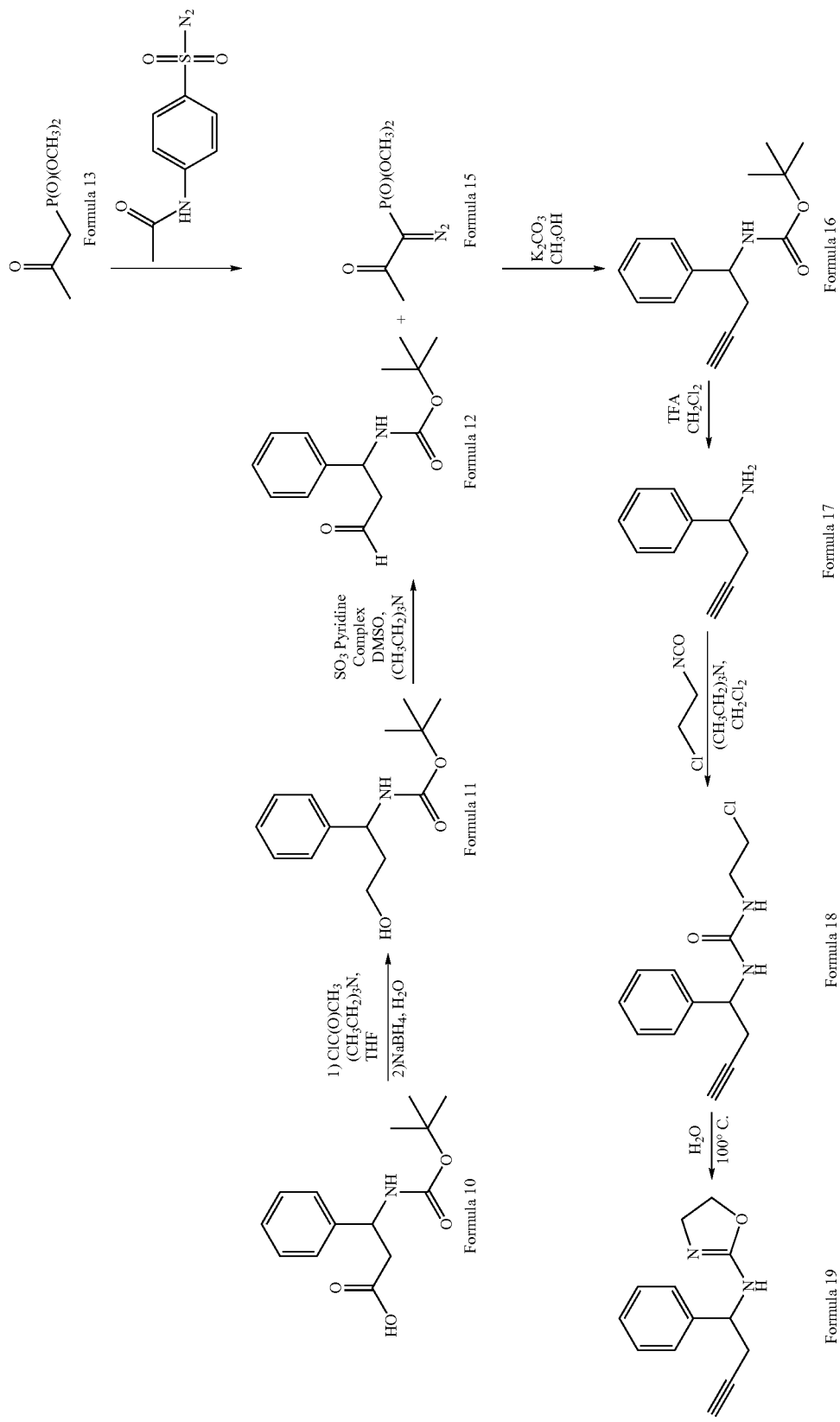

A. Synthesis of tert-butyl-3-hydroxy-1-phenylpropylcarbamate

To a 17.9 mmol suspension of 3-(tert-butoxycarbonylamino)-3-phenylpropanoic acid (Formula 10) in tetrahydrofuran (THF) at 0° C. was added 2.74 mL of triethyl amine and 1.52 mL of methyl chloroformate. The mixture was stirred at 0° C. for 15 minutes. Next, the white solid formed was filtered off and washed with 10 mL of THF. The filtrate was added drop-wise to 8.4 mL of 26.8 mmol sodium borohydride at 0° C. and stirred for 30 min. The mixture was then stirred at room temperature for 2 hr. Ten percent hydrochloric acid (HCl) was added until a pH of 2 was reached, and then was extracted using ethyl acetate. The resulting combined ethyl acetate layers were washed with sodium carbonate, water, brine, and concentrated. Column chromatography (50% ethyl acetate/hexane) gave 1.63 g (36%) of the title compound as a colorless oil. The aqueous phase was acidified with HCl and extracted with ethyl acetate to recover 2 g of 3-(tert-butoxycarbonylamino)-3-phenylpropanoic acid. $^1$H NMR (300 MHz, CDCl$_3$) δ 1.45 (s, 9H), 1.62-1.63 (m, 1H), 1.79-1.87 (m, 1H), 3.68-3.74 (m, 2H), 5.23 (br, 1H), 5.32 (br, 1H), 7.26-7.38 (m, 5H).

B. Synthesis of tert-butyl-3-oxo-1-phenylpropylcarbamate

To a solution of 1.63 g of tert-butyl 3-hydroxy-1-phenylpropylcarbamate (Formula 11) in 15 mL of dimethyl sulfoxide (DMSO) was added 2.72 mL of triethylamine. The solution was cooled to 0° C. and 3.1 g of sulfur trioxide pyridine complex in 15 mL of DMSO was added. The reaction mixture was stirred at room temperature for 1 hour then poured onto ice-water and extracted with ethyl acetate. The combined ethyl acetate layers were washed with 10% acetic acid, water, 5% sodium bicarbonate, and brine, dried over sodium sulfate and concentrated. Column chromatography (40% ethyl acetate/hexane) gave 1.2 g (74%) of tert-butyl-3-oxo-1-phenylpropylcarbamate (Formula 12) as a white solid. $^1$H NMR (300 MHz, CDCl$_3$) δ 1.43 (s, 9H), 2.89-2.96 (m, 2H), 5.23 (br, 1H), 5.32 (br, 1H), 7.27-7.37 (m, 5H), 9.74 (m, 1H).

C. Synthesis of dimethyl 1-diazo-2-oxopropylphosphonate

To a suspension of 4.1 g of NaH (washed with hexane) in 110 mL of benzene and 25 mL of THF at 5° C., was added 15.5 g of dimethyl 2-oxopropylphosphonate (Formula 13) in 15 mL of benzene. The resulting solution was stirred at 5-10° C. for 1 hour. A solution of 24.7 g of 4-acetamidobenzenesulfonyl azide (Formula 14) in 25 mL of benzene and 50 mL of THF was then added and the mixture was stirred at room temperature for 2 hours. The yellow suspension was filtered through celite and washed with ethyl ether. The filtrate was concentrated to give 18 g of dimethyl 1-diazo-2-oxopropylphosphonate (Formula 15) as a light yellow oil.

D. Synthesis of tert-butyl 1-phenylbut-3-ynylcarbamate

To the solution of 1.2 g of tert-butyl 3-oxo-1-phenylpropylcarbamate (Formula 12) and 1.38 g of dimethyl 1-diazo-2-oxopropylphosphonate (Formula 15) in 60 mL of methanol at 0° C. was added 1.32 g of potassium carbonate. The mixture was stirred at room temperature for 16 hours then quenched with saturated ammonium chloride solution and extracted with ethyl acetate. The combined organic layers were washed with brine, dried over sodium sulfate and concentrated. Column chromatography (5% ethyl acetate/hexane) gave 1.03 g (87%) of tert-butyl 1-phenylbut-3-ynylcarbamate (Formula 16) as a white solid. $^1$H NMR (300 MHz, CDCl$_3$) δ 1.43 (s, 9H), 1.98-2.00 (m, 1H), 2.6-2.8 (m, 2H), 4.88 (br, 1H), 5.16 (br, 1H), 7.23-7.37 (m, 5H).

E. Synthesis of 1-phenylbut-3-yn-1-amine

To a solution of 1.03 g of tert-butyl 1-phenylbut-3-ynylcarbamate (Formula 16) in 15 mL of dichloromethane was added 3 mL of trifluoroacetic acid. The mixture was stirred at room temperature for 1 hour. Then, dichloromethane was removed. The residue was diluted with water and extracted with ethyl acetate. Combined ethyl acetate was washed with brine, dried over sodium sulfate and concentrated. Column chromatography (60% ethyl acetate/hexane) gave 564 mg (93%) of 1-phenylbut-3-yn-1-amine (Formula 17) as a clear oil. $^1$H NMR (300 MHz, CDCl$_3$) δ 2.04-2.05 (m, 1H), 2.43-2.63 (m, 2H), 4.14-4.19 (m, 1H), 7.24-7.40 (m, 5H).

F. Synthesis of 1-(2-chloroethyl)-3-(1-phenylbut-3-ynyl)urea

To a solution of 187 mg of 1-phenylbut-3-yn-1-amine (Formula 17) in 5 mL of dichloromethane was added 0.16 mL of 2-chloroethyl isocyanate and 0.26 mL of triethylamine. The mixture was stirred at room temperature for 2 hours. Then, dichloromethane was removed. Column chromatography (3% methanol/dichloromethane) followed by recrystallization from chloroform to give 25 mg of 1-(2-chloroethyl)-3-(1-phenylbut-3-ynyl)urea (Formula 18) as a white solid and 200 mg of impure material which was used without further purification. $^1$H NMR (300 MHz, CDCl$_3$) δ 2.02-2.04 (m, 1H), 2.64-2.82 (m, 2H), 3.49-3.61 (m, 4H), 4.80 (br, 1H), 4.92-5.05 (m, 2H), 7.26-7.37 (m, 5H)

G. Synthesis of N-(1-phenylbut-3-ynyl)-4,5-dihydrooxazol-2-amine

A solution of 200 mg of 1-(2-chloroethyl)-3-(1-phenylbut-3-ynyl)urea (Formula 18) in 5 mL of water was heated at 100° C. for 2.5 hours. The reaction mixture was cooled to room temperature. Then, a saturated solution of sodium carbonate was added until the pH of the solution was greater than 8. The mixture was extracted with ethyl acetate. Combined ethyl acetate was washed with brine, dried over sodium sulfate and concentrated. Column chromatography (4% 7N NH$_3$ in CH$_3$OH/CH$_2$Cl$_2$) gave 54 mg of N-(1-phenylbut-3-ynyl)-4,5-dihydrooxazol-2-amine (Formula 19) as a white solid. $^1$H NMR (300 MHz, CDCl$_3$) δ 1.98-2.00 (m, 1H), 2.66-2.84 (m, 2H), 3.68-3.76 (m, 2H), 4.20-4.26 (m, 2H), 4.83-4.87 (m, 1H), 7.25-7.39 (m, 5H).

EXAMPLE 2

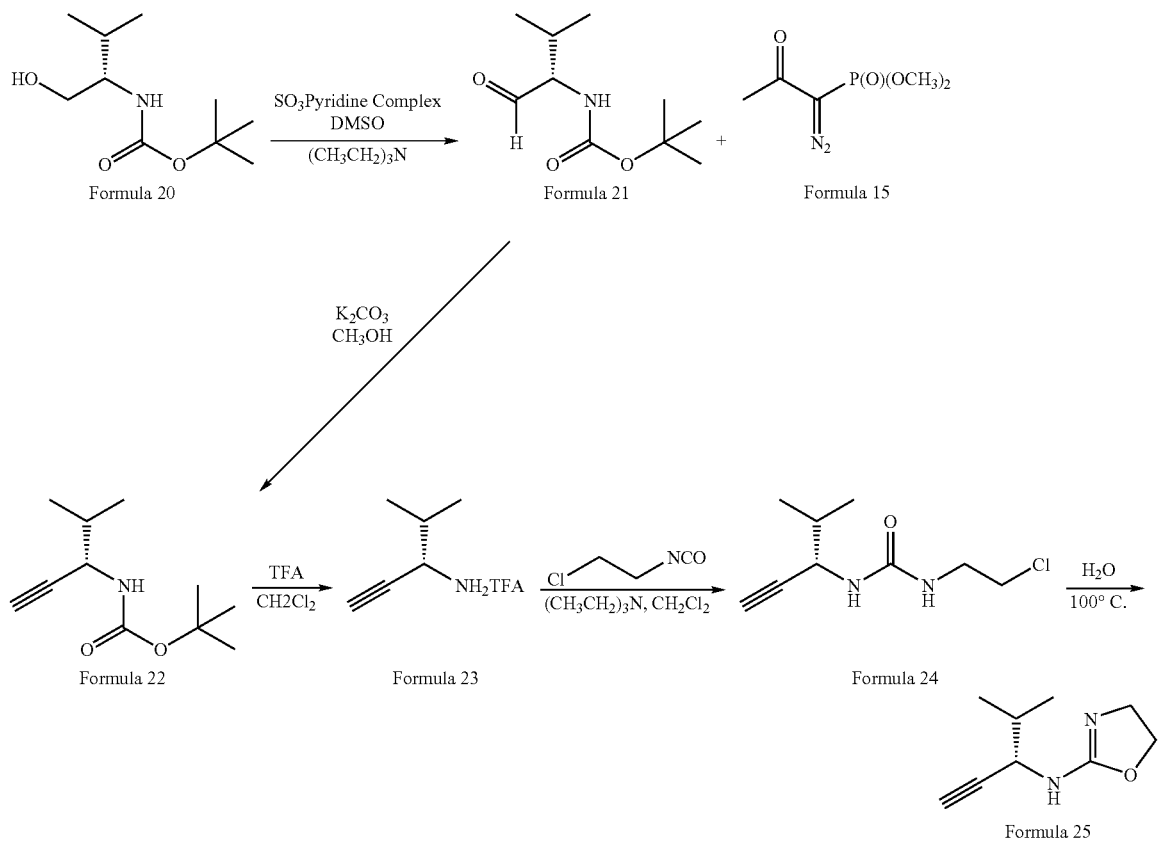

A. Synthesis of tert-butyl 3-methyl-1-oxobutan-2-ylcarbamate

To a solution of 1.75 g of tert-butyl 1-hydroxy-3-methylbutan-2-ylcarbamate (Formula 20) in 25 mL of DMSO was added 3.6 mL of triethylamine. The solution was cooled to 0° C. and 4.1 grams of sulfur trioxide pyridine complex in 25 mL of DMSO was added. The reaction mixture was stirred at room temperature for 1 hour. Then, the mixture was poured onto ice-water and extracted with ethyl acetate. The organic layers were washed with 10% acetic acid, water, 5% sodium bicarbonate, and brine, dried over sodium sulfate and concentrated. Column chromatography (30% ethyl acetate/hexane) gave 1.25 g of tert-butyl 3-methyl-1-oxobutan-2-ylcarbamate (Formula 21) as a clear oil. $^1$H NMR (300 MHz, CDCl$_3$) δ 0.95 (d, J=7.32 Hz, 3H), 1.03 (d, J=6.83 Hz, 3H), 1.45 (s, 9H), 2.27-2.29 (m, 1H), 4.24-4.26 (m, 1H), 9.65 (s, 1H).

B. Synthesis of tert-butyl 4-methylpent-1-yn-3-ylcarbamate

To a solution of 1.25 g of tert-butyl 3-methyl-1-oxobutan-2-ylcarbamate (Formula 21) and 1.79 g of dimethyl 1-diazo-2-oxopropylphosphonate (Formula 15) in 80 mL of methanol at 0° C. was added 1.72 g of potassium carbonate. The mixture was stirred at room temperature for 16 hours then quenched with saturated ammonium chloride solution and extracted with ethyl acetate. The combined organic layers were washed with brine, dried over sodium sulfate and concentrated. Column chromatography (15% ethyl acetate/hexane) gave 1.01 g of tert-butyl 4-methylpent-1-yn-3-ylcarbamate (Formula 22) as a clear oil. $^1$H NMR (300 MHz, CDCl$_3$) δ 0.98-1.00 (m, 6H), 1.45 (s, 9H), 1.87-1.93 (m, 1H), 2.24-2.25 (m, 1H), 4.32 (br, 1H).

C. Synthesis of 4-methylpent-1-yn-3-amine

To a solution of 1.01 g of tert-butyl 4-methylpent-1-yn-3-ylcarbamate (Formula 22) in 20 mL of dichloromethane was added 4 mL of trifluoroacetic acid (TFA). After the mixture was stirred at room temperature for 1 hour, concentration gave 1.1 g of 4-methylpent-1-yn-3-amine (Formula 23) as a pale yellow oil. This was used directly in the next step without further purification. $^1$H NMR (300 MHz, CDCl$_3$) δ 1.07-1.11 (m, 6H), 2.09-2.18 (m, 1H), 2.53-2.54 (m, 1H), 3.86-3.89 (m, 1H).

D. Synthesis of 1-(2-chloroethyl)-3-(4-methylpent-1-yn-3-yl)urea

To a solution of 256 mg of 4-methylpent-1-yn-3-amine (Formula 23) in 10 mL of dichloromethane was added 0.5 mL of 2-chloroethyl isocyanate and 0.5 mL of triethylamine. After the mixture was stirred at room temperature for 2 hours, the solvent was removed and column chromatography (40% ethyl acetate/hexane) gave 210 mg of 1-(2-Chloroethyl)-3-(4-methylpent-1-yn-3-yl)urea (Formula 24) as a white solid.

$^1$H NMR (300 MHz, CDCl$_3$) δ 0.95-1.01 (m, 6H), 1.84-1.93 (m, 1H), 2.25-2.26 (m, 1H), 3.51-3.63 (m, 4H), 4.40-4.45 (m, 1H).

E. Synthesis of N-(4-methylpent-1-yn-3-yl)-4,5-dihydrooxazol-2-amine

A solution of 169 mg of 1-(2-chloroethyl)-3-(4-methylpent-1-yn-3-yl)urea (Formula 24) in 10 mL of water was heated at 100° C. for 2.5 hours. The reaction mixture was cooled to room temperature. Then, a saturated solution of sodium carbonate was added to adjust the pH of the solution to greater than 8. The mixture was extracted with ethyl acetate. The combined ethyl acetate was washed with brine, dried over sodium sulfate and concentrated. Column chromatography (5% 7N NH$_3$ in MeOH/CH$_2$Cl$_2$) gave 60 mg of N-(4-methylpent-1-yn-3-yl)-4,5-dihydrooxazol-2-amine (Formula 25) as a white solid. $^1$H NMR (300 MHz, CDCl$_3$) δ 1.01 (m, 6H), 1.95-2.02 (m, 1H), 2.28-2.29 (m, 1H), 3.76-3.83 (m, 2H), 4.24-4.32 (m, 3H).

EXAMPLE 3

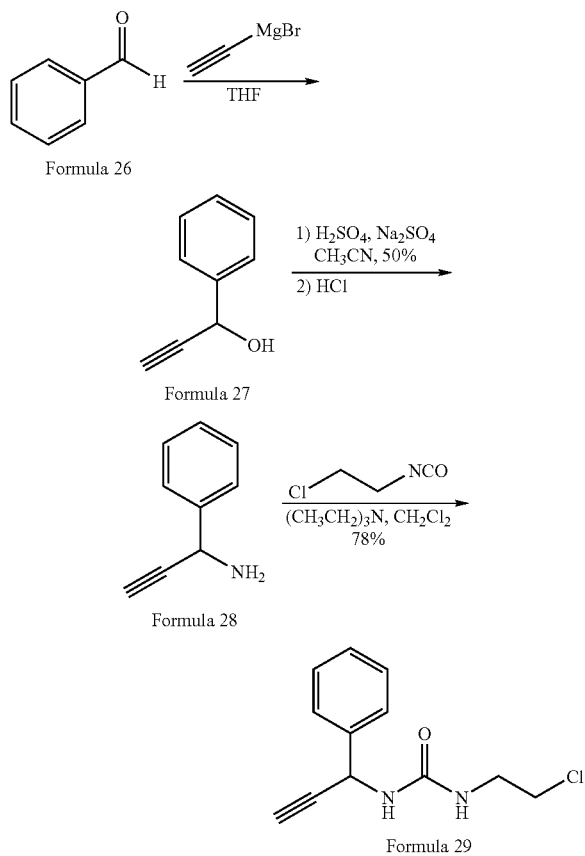

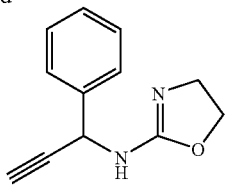

Formula 30

A. Synthesis of 1-phenyl-prop-2-yn-1-ol

To a solution of 2.65 g of benzaldehyde (Formula 26) in 50 mL of THF at room temperature was added 100 mL of 0.5M ethynylmagnesium bromide in THF. The mixture was stirred at room temperature for 2 hours. Then, the mixture was diluted with diethylether and a saturated solution of ammonium chloride. The mixture was extracted with ethyl acetate. Combined ethyl acetate was washed with brine, dried over sodium sulfate and concentrated. Column chromatography (20% ethyl acetate/hexane) gave 3.17 g of 1-phenyl-prop-2-yn-1-ol (Formula 27) as a light yellow oil. $^1$H NMR (300 MHz, CDCl$_3$) δ 2.68 (m, 1H), 5.46-5.49 (m, 1H), 7.34-7.43 (m, 3H), 7.55-7.57 (m, 2H).

B. Synthesis of 1-phenyl-prop-2-ynylamine

To a mixture of 1.78 g of 1-phenyl-prop-2-yn-1-ol (Formula 27) and 1.92 g of sodium sulfate in 22 mL of acetonitrile at −25° C. was added drop-wise, a solution of 6.68 g of sulfuric acid in 15 mL of acetonitrile. The mixture was stirred while the temperature was ramped from −25° C. to room temperature over 30 min. The mixture was then poured onto ice-water. The mixture was extracted with ethyl acetate. Combined ethyl acetate was washed with brine, dried over sodium sulfate and concentrated. Column chromatography (40% ethyl acetate/hexane) gave 1.43 g of a white solid.

To 1.43 g of the above white solid in 30 mL of THF was added 25 mL of 3.5M HCl. The mixture was heated at 95° C. for 5 hours. Then, the mixture was cooled to room temperature. The acidic mixture was washed with ethyl acetate and then added sodium hydroxide until the pH was greater than 10. The basic mixture was extracted with ethyl acetate. Combined ethyl acetate was washed with brine, dried over sodium sulfate and concentrated. Column chromatography (50% ethyl acetate/hexane) gave 625 mg of 1-phenyl-prop-2-ynylamine (Formula 28) as a light brown oil. $^1$H NMR (300 MHz, CDCl$_3$) δ 2.49 (d, J=2.1 Hz, 1H), 4.78 (d, J=2.1 Hz, 1H), 7.27-7.319 (m, 3H), 7.53-7.55 (m, 2H).

C. Synthesis of 1-(2-chloro-ethyl)-3-(1-phenyl-prop-2-ynyl)-urea

To a solution of 180 mg of 1-phenyl-prop-2-ynylamine (Formula 28) in 5 mL of CH$_2$Cl$_2$ were added 0.1 mL of 2-chloroethyl isocyanate and 0.2 mL of triethylamine. After the mixture was stirred at room temperature for 2 hours, the solvent was removed. Column chromatography (50% ethyl acetate/hexane) gave 153 mg of 1-(2-chloro-ethyl)-3-(1-phenyl-prop-2-ynyl)-urea (Formula 29) as a white solid. $^1$H NMR (300 MHz, CDCl$_3$) δ 2.46 (m, 1H), 3.45-3.49 (m, 2H), 3.52-3.54 (m, 2H), 5.40-5.41 (m, 1H), 5.55-5.57 (m, 1H), 5.74-5.76 (m, 1H), 7.27-7.35 (m, 3H), 7.48-7.50 (m, 2H).

D. Synthesis of (4,5-dihydro-oxazol-2-yl)-(1-phenyl-prop-2-ynyl)-amine

A solution of 136 mg of 1-(2-chloro-ethyl)-3-(1-phenyl-prop-2-ynyl)-urea (Formula 29) in 5 mL of water was heated at 100° C. for 2.5 hours. The reaction mixture was cooled to room temperature. Then, sodium carbonate (saturated solution) was added to the mixture until the pH was greater than 8. The mixture was extracted with ethyl acetate. Combined ethyl acetate was washed with brine, dried over sodium sulfate and concentrated. Column chromatography (3-5% 7N $NH_3$ in $MeOH/CH_2Cl_2$) gave 84 mg of (4,5-Dihydro-oxazol-2-yl)-(1-phenyl-prop-2-ynyl)-amine (Formula 30) as a white solid. $^1H$ NMR (300 MHz, $CDCl_3$) δ 2.49 (d, J=2.0 Hz, 1H), 3.66-3.75 (m, 2H), 4.22-4.28 (m, 2H), 5.58 (d, J=2.0 Hz, 1H), 7.26-7.31 (m, 1H), 7.33-7.36 (m, 2H), 7.52-7.54 (m, 2H).

EXAMPLE 4

A nasal spray comprising formula 1 is administered to a patient 5 times a day until the symptoms subside. The amount administered is an amount that is determined by one skilled in the art as being therapeutically effective. In another embodiment, the nasal spray can be delivered more than 5 times a day, depending on the dose.

EXAMPLE 5

A capsule containing a formulation comprising a compound of formula 1 is administered once daily to a patient suffering from osteoporosis. The amount administered is an amount that is determined by one skilled in the art as being therapeutically effective. In other embodiments depending on the dose, the capsule may be administered more than once per day. An increase in bone density or a reduction of bone density loss occurs as the patient continues treatment.

EXAMPLE 6

A capsule containing a formulation comprising a compound of formula 1 is administered to a patient suffering from a migraine. The amount administered is an amount that is determined by one skilled in the art as being therapeutically effective. Significantly less pain is experienced after administration to the patient.

EXAMPLE 7

A capsule containing a formulation comprising a compound of formula 1 is administered once daily to a patient suffering from cancer. The amount administered is an amount that is determined by one skilled in the art as being therapeutically effective. In other embodiments depending on the dose, the capsule may be administered more than once per day. An improvement in the patient's condition occurs after administration.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compound for administration to a mammal represented by the formula 1:

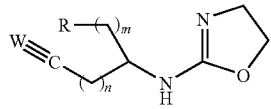

Formula 1 wherein n is 0 or 1; m is 0 or 1-3; W is CH or N; R is a $C_{1-10}$ alkyl 2, 3-difluorophenyl, 3-chlorophenyl, 2-bromophenyl, or phenyl; and pharmaceutically acceptable salts, and combinations thereof.

2. The compound according to claim 1, wherein said compound is selected from the group consisting of:

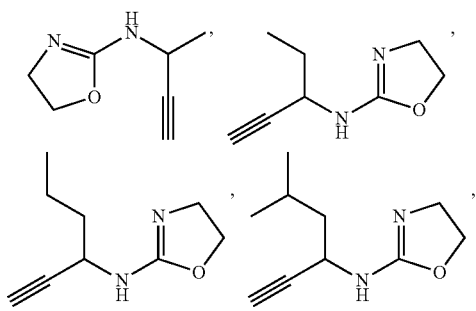

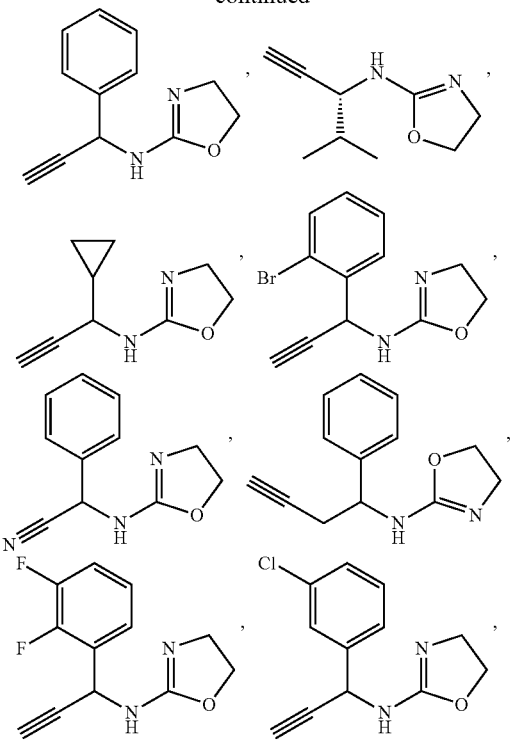

salts, and combinations thereof.

* * * * *